United States Patent [19]

Chu et al.

[11] Patent Number: 6,001,232
[45] Date of Patent: Dec. 14, 1999

[54] SEPARATION MEDIUM FOR CAPILLARY ELECTROPHORESIS

[75] Inventors: Benjamin Chu, Setauket; Chunhung Wu, Lake Grove, both of N.Y.

[73] Assignee: The Research Foundation of State University of New York, Albany, N.Y.

[21] Appl. No.: 08/707,794

[22] Filed: Sep. 4, 1996

[51] Int. Cl.⁶ .......................... G01N 27/26; G01N 27/447
[52] U.S. Cl. .......................... 204/455; 204/489; 204/605
[58] Field of Search ........................... 204/489, 455, 204/605

[56] References Cited

U.S. PATENT DOCUMENTS

| | | | |
|---|---|---|---|
| 4,582,868 | 4/1986 | Ogawa et al. | 204/469 |
| 4,680,201 | 7/1987 | Hjerten | 204/601 |
| 4,769,408 | 9/1988 | Ogawa et al. | 204/469 |
| 4,812,269 | 3/1989 | Harttig et al. | 264/41 |
| 4,865,707 | 9/1989 | Karger et al. | 204/605 |
| 4,990,558 | 2/1991 | DeNicola, Jr. et al. | 524/504 |
| 5,126,021 | 6/1992 | Grossman | 204/601 |
| 5,143,646 | 9/1992 | Nochumson et al. | 204/469 |
| 5,151,464 | 9/1992 | Yang | 524/449 |
| 5,164,055 | 11/1992 | Dubrow | 204/455 |
| 5,167,784 | 12/1992 | Noolandi | 204/458 |
| 5,213,669 | 5/1993 | Guttman | 204/605 |
| 5,264,101 | 11/1993 | Demorest et al. | 204/452 |
| 5,282,941 | 2/1994 | Rose, Jr. | 204/605 |
| 5,290,418 | 3/1994 | Menchen et al. | 204/455 |
| 5,306,501 | 4/1994 | Yiegas et al. | 424/423 |
| 5,360,855 | 11/1994 | Gobran | 524/274 |
| 5,447,617 | 9/1995 | Shieh | 204/451 |
| 5,468,365 | 11/1995 | Menchen et al. | 204/455 |
| 5,631,337 | 5/1997 | Sassi et al. | 526/307.2 |

FOREIGN PATENT DOCUMENTS 6-273382 9/1994 Japan.

OTHER PUBLICATIONS

Martin Malmsten et al, "Adsorption of PEO–PPO–PEO Block Copolymers at Silica" Macromolecules, vol. 35, No. 9, pp. 2474–2481, 1992, no month available.

Hiroshi Yoshioka et al, "A synthetic hydrogel with thermo reversible gelation. I. Preparation and rheological properties" J. Macromol. Sci., Pure Appl. Chem. A 31(1) 113–20, 1994, no month available.

Chu, B., *Langmuir* 1995, 11, 414–421, no month available.

*Primary Examiner*—Jill Warden
*Assistant Examiner*—John S. Starsiak, Jr.
*Attorney, Agent, or Firm*—Hoffmann & Baron, LLP

[57] ABSTRACT

A viscosity-adjustable medium for use in separation methods is described. In particular, a block copolymer composition is described which exists as a low viscosity solution at a temperature outside of the temperature range of electrophoresis and which self-assembles into a gel-like polymer network at electrophoresis operating temperatures. A system is described for conducting molecular separation in a capillary column using the viscosity-adjustable medium. In addition, a method is also described for separating charged molecules.

18 Claims, 6 Drawing Sheets

SEPARATION MEDIUM FOR CAPILLARY ELECTROPHORESIS

The present invention has resulted from investigatory work supported by U.S. Government funds provided under NIH: National Center for Genome Research (1R01HG0138601); ARO: U.S. Army Research Office (ARO-DAAH0494G0053); and Biotechnology Center of the State of New York (X310N). The government has certain rights in the invention.

BACKGROUND OF THE INVENTION

The present invention relates generally to the art of separating charged molecular species, and, in particular, to new compositions and methods for practicing same.

Capillary gel electrophoresis is one of the most widely used separation techniques in the biologically related sciences. Charged molecular species such as proteins, peptides, nucleic acids, amino acids and oligonucleotides are separated by causing the species to migrate in a buffer medium under the influence of an electric field. The buffer medium normally is used in conjunction with a low to moderate concentration of an appropriate gelling agent, such as for example, agarose or cross-linked polyacrylamide, to promote the separation and to minimize the occurrence of mixing of the species being separated.

Until recently, electrophoretic separations were conducted in gel slabs or open gel beds which were typically fabricated of agarose or cross-linked polyacrylamide material. More recently, capillary gel electrophoresis techniques combined with photometric detection methods have allowed the automation and rapid quantitative analysis of charged molecules. Furthermore, capillary gel electrophoresis can provide quantitative information about a sample using very small amounts of the sample, gel and buffer relative to traditional slab gel processes. Moreover, high resolution separation of molecules having different effective charges have been achieved by applying electrophoretic principles to polymer solution filled or gel filled narrow capillary tubes.

Typically, the capillary columns used in capillary gel electrophoresis are fabricated from lengths of fused silica tubing having diameters on the order of 25 $\mu$m to 200 $\mu$m and lengths from about 30 cm to about 200 cm. The buffer and gel separation media are pumped directly into the column interiors and electrophoretic techniques are used to separate charged molecular species.

A major drawback to the use of such capillary gel electrophoresis methods, however, is the inability of many separation media to bind directly to the inner wall of capillary tubes. The inability of a separation medium to bind to the inner wall of a fused silica capillary tube which is negatively charged creates an electro-osmotic flow when an electric field is applied during electrophoresis. Such migration does not provide a satisfactory separation of the constituent parts of a sample.

Accordingly, traditional methods aimed at preventing electro-osmosis include introducing a compound which binds to the inner surface of a capillary tube wall, as well as, to the separation medium prior to injecting the separation medium into the tube. For example, U.S. Pat. No. 5,447,617 to Shieh describes covalently bonding polybutadiene to the inner surface of a capillary tube, introducing polyacrylamide therein and co-polymerizing the polyacrylamide with the polybutadiene. Such precoating techniques, however, are time consuming, inconvenient and costly.

A further problem of conventional capillary gel electrophoresis is encountered with the use of polyacrylamide-based separation media. Such media are injected into the capillary tube in unpolymerized form. Polymerization of the polyacrylamide is then induced within the capillary tube by any number of methods including ultraviolet radiation and chemical catalysts. Such methods are characterized by a lack of uniformity in the pore size distribution of the polymer network formed, and by incomplete polymerization.

A still further problem encountered with the use of polyacrylamide-based separation media in capillary gel electrophoresis methods relates to the irreversible nature of the polymerized polyacrylamide gel. Once the polyacrylamide is polymerized within a capillary electrophoresis tube, the polymerized gel is very difficult to remove from the capillary tube after electrophoresis. Furthermore, isolation of the separated constituents of a sample from the polymerized polyacrylamide gel is very difficult because of the polymerized gel.

Accordingly, attempts have been made to use nonpolymerized separation media for capillary gel electrophoresis. For example, U.S. Pat. No. 5,126,021 to Grossman describes a capillary electrophoresis (CE) element composed of an uncharged, water-soluble polymer in a low-viscosity solution. The polymers within this solution form entanglements which create a mesh size that is suitable for electrophoretic separation of charged molecules. This CE element remains liquid during the electrophoretic separation of a sample which allows for easy removal of the element from the capillary tube. The Grossman '021 patent, however, requires that a coating be deposited onto the inner surface of the capillary tube prior to introduction of the electrophoresis element in order to prevent electro-osmotic flow. As set forth hereinabove, such a precoating is time consuming, inconvenient and costly.

Similarly, U.S. Pat. No. 5,468,365 to Menchen et al. describes an electrophoresis medium having a matrix of aggregated copolymers dispersed in an aqueous medium. The polymer matrix of the '365 patent is described as a dispersion of one substance (micelles) in another (water). In such a dispersion, the particles are formed by the association or aggregation of molecules having both hydrophilic and hydrophobic regions. The copolymers of the '365 patent form a polymer matrix having a relatively uniform mesh size which is believed to be related to the regular, i.e., substantially uniform spacing between adjacent hydrophobic polymer segments. The separation matrix of the '365 patent, however, exists only in one phase (liquid) and is accordingly difficult to manipulate.

Accordingly, it would be desirable to provide a new separation medium for electrophoresis methods that does not require coating of the inner cavity of a capillary tube. It would also be desirable to provide a new separation medium with the ability to change between liquid and gel-like states for efficient application and removal of the medium from electrophoresis apparatus. In particular, it would be desirable to provide a viscosity-adjustable medium for use in separation methods which is easy to apply and remove from various apparatus, and from which it is easy to isolate components of an electrophoretically separated sample.

SUMMARY OF THE INVENTION

The present invention includes a method for separating charged molecules and a viscosity-adjustable medium for use in separation methods. The viscosity-adjustable medium includes at least one block copolymer which is in solution at a first operating temperature and is in a gel-like state at a second operating temperature. The viscosity-adjustable medium of the present invention further includes an operating buffer which dissolves block copolymers at the first operating temperature and remains in the medium in the gel-like state without disruption of the separation method. This buffer renders the block copolymers of the present invention dissolute upon return to the first operating temperature.

Another embodiment of the present invention is a system for conducting molecular separation which includes a capillary column having an interior cavity defined by a wall with an inner surface, and a viscosity-adjustable medium as described above within the interior cavity of the capillary column.

Although at least one block copolymer of the viscosity-adjustable medium is required to practice the present invention, at least one additional block copolymer may be added thereto. Furthermore, the block copolymers of the present invention may be selected from di-block copolymers, tri-block copolymers, multi-block copolymers and mixtures thereof. Moreover, these block copolymers are further defined by the following formulae: (I) $A_xB_y$; (II) $A_xB_yA_z$; (III) $B_xA_yB_z$; (IV) $A_xB_yC_z$; and mixtures thereof wherein A, B and C are independently selected from the group consisting of poly(oxyethylene), poly(oxypropylene), poly(oxybutylene), polyacrylamide and poly(isopropyl) acrylamide; and x, y, and z are independently selected from whole numbers from about 1–10,000.

Preferably, at least one of the block copolymers is $E_{41}B_8$, $E_{99}P_{69}E_{99}$, $B_{12}E_{260}B_{12}$, $E_{45}B_{14}E_{45}$, $E_{132}P_{56}E_{132}$, $E_{79}B_{36}E_{79}$, and mixtures thereof wherein E is poly(oxyethylene), P is poly(oxypropylene) and B is poly(oxybutylene).

As stated hereinabove, the viscosity-adjustable medium includes an operating buffer. Preferably, the operating buffer is, for example, a good solvent for a first block segment of the block copolymer and is a marginal, a poor or a nonsolvent for a second block of the block copolymer. In such a buffer, the marginally solvated, poorly solvated, or nonsolvated block segments of the block copolymer self-assemble. Preferred operating buffers can include components such as tris(hydroxymethyl)-aminomethane, 2-N-(morpholine) ethanesulfonic acid, N-(2-acetamido)iminodiacetic acid, piperazine-N,N'-bis(2-ethanesulfonic acid, N(2-acetamido)-2-aminoethanesulfonic acid, (2-aminoethyl) trimethyl-ammonium chloride hydrochloride, N,N-bis(2-hydroxyethyl)-2-aminoethane sulfonic acid, N-2-hydroxyethylpiperazine-N'-2-ethanesulfonic acid, N-tris(hydroxylmethyl)methylglycine, N,N-bis(2-hydroxyethyl)-glycine, 2-(N-cyclohexylamino)ethanesulfonic acid and mixtures thereof. A more preferred operating buffer is 1× TBE buffer which includes about 89 mM tris(hydroxymethyl) aminomethane, about 89 mM boric acid and about 2 mM EDTA in deionized water. A preferred viscosity-adjustable medium of the present invention includes, for example, about 25% (w/v) of $E_{99}P_{69}E_{99}$ in 1× TBE buffer.

Preferably, the first operating temperature is outside of the operative temperature for electrophoresis; whereas, the second operating temperature is about at the operative temperature for electrophoresis. More preferably, the first operating temperature is from about 15° C. to about 1° C.; whereas, the second operating temperature is above about 20° C.

In the present invention, the separation methods can include, for example, capillary electrophoresis and thin-slab electrophoresis.

As a result of the present invention, separation media are quickly and efficiently introduced to, and removed from, for example, capillary electrophoresis columns. The method of the invention is economical and can be readily integrated into existing systems. Because the separation media contain block copolymers that can bind to the inner walls of capillary tubes, precoating the capillary tubes prior to introduction of the present separation medium is unnecessary. Furthermore, the viscosity-adjustable nature of the present separation media allows for the quick and efficient isolation and retrieval of electrophoretically separated components.

These and other advantages will become apparent to the skilled artisan in view of the disclosure set forth herein.

DETAILED DESCRIPTION OF THE PREFERRED EMBODIMENTS

The present invention includes a viscosity-adjustable medium for use in separation methods, which relies on at least one block copolymer in an operating buffer. For purposes of the present invention, "viscosity-adjustable medium" refers to a solution containing one or more of the block copolymers described hereinbelow in a selective operating buffer which is a good solvent for one of the segments of the block copolymer but a marginal solvent, a poor solvent or a nonsolvent for another of the segments of the block copolymer at the operative temperature for electrophoresis. By varying the temperature of the block copolymers of the present invention, the present viscosity-adjustable medium is able to change its physical structure between a low viscosity solution and a gel-like matrix.

In particular, at a first operating temperature the block copolymer solution of the present invention has a low solution viscosity which makes it very easy to dispense the solution into, for example, capillary tubes or thin slabs. In addition, when the separation media of the present invention are in their low solution viscosity state, they are easily manipulatable using, for example, pipettes and syringes.

For purposes of the present invention, "gel-like state" means a state which has the appearance and consistency of a gel but is further characterized by the ability of the block copolymers within the separation medium to dynamically self-assemble and disassemble wherein substantially all of the block copolymers are self-assembled at any one time. In the self-assembled state, the block copolymers form gel-like networks with predetermined microstructures which are suitable for separation of charged molecules.

As used in the present invention, "first operating temperature" refers to a temperature which is not destructive of the block copolymer medium of the present invention and which is characterized by a low solution viscosity of the block copolymer medium. At such a low solution viscosity, the block copolymer medium can be easily introduced into various pieces of equipment without destruction of the block copolymers. "Second operating temperature" as used in the present invention means a temperature at which the block copolymer medium of the present invention exists in a gel-like state which is able to provide the desired separation of charged molecules. This second operating temperature does not destroy the block copolymer medium or the sample; nor does it prevent the block copolymer medium from returning to the low solution viscosity state. Thus, by changing the temperature of the block copolymer medium of the present invention between the first operating temperature and the second operating temperature, the viscosity and structure of the medium can be adjusted between a low viscosity solution and a gel-like matrix.

As set forth hereinabove, the block copolymers of the present invention are characterized by their ability to self-assemble into a gel-like matrix which is suitable for, e.g., separation of charged molecules during electrophoresis. The structure and properties of these block copolymers can vary depending upon the total chain length, the block length ratio, the block sequence, and the buffer. For example, a variety of self-assembled structures can be created with the block copolymers of the invention which range from core/shell micelles, such as for example AB or ABA block copolymers or flower-like micelles, such as for example BAB tri-block copolymers to branched and network-like structures, such as for example, BAB tri-block copolymers having a long middle soluble A block.

For purposes of the present invention, "operating buffer" means a solution that is a good solvent for one of the block segments of the block copolymer but is a marginal solvent, a poor solvent or a nonsolvent for another block segment. Furthermore, the operating buffer of the present invention must not destroy either the block copolymers dissolved therein or the sample to be separated. Moreover, the operating buffer must remain functional at both the first and second operating temperatures. By "functional" it is meant that the buffer retains its ability to dissolve the copolymers at the first operating temperature and does not interfere with the ability of the block copolymers to self-assemble into the gel-like state at the second operating temperature.

In accordance with another embodiment of the present invention, the viscosity-adjustable medium may contain at least one additional block copolymer. The block copolymers of the present invention can be any block copolymer that is capable of forming a viscosity-adjustable medium in an operating buffer. Preferred block copolymers include for example, di-block copolymers, tri-block copolymers and mixtures thereof.

The viscosity-adjustable medium of the present invention contains at least one block copolymer which may be described by the following formulae:

$A_xB_y$;  Formula (I)

$A_xB_yA_z$;  Formula (II)

$B_xA_yB_z$;  Formula (III)

$A_xB_yC_z$;  Formula (IV)

and mixtures thereof, wherein A, B and C are independently selected from the group consisting of poly (oxyethylene), poly(oxypropylene), poly (oxybutylene), polyacrylamide and poly(isopropyl) acrylamide; and x, y, and z are independently selected from whole numbers from about 1–10,000.

The following group of copolymers (Group A) have been found to be especially good at separating low molecular weight DNA fragments using capillary electrophoretic techniques: 25% $E_{99}P_{69}E_{99}$; 10% $B_{12}E_{260}B_{12}$; 5% $B_{12}E_{260}B_{12}$+ 5% $E_{41}B_8$; 5% $B_{12}E_{260}B_{12}$+5% $E_{45}B_{14}E_{45}$; 5% $B_{12}E_{260}B_{12}$+10% $E_{41}B_8$. A second group of block copolymers (Group B) of the present invention have exhibited the ability to separate DNA during capillary electrophoresis but at a lower resolution than the Group A copolymers. These Group B block copolymers include 30% $E_{132}P_{56}E_{132}$; 15% $E_{79}B_{36}E_{79}$; 20% $E_{79}B_{36}E_{79}$; and 5% $B_{12}E_{260}B_{12}$+ 5%$E_{79}B_{36}E_{79}$. A third group of block copolymers (Group C) of the present invention have demonstrated marginal to no ability to separate DNA during capillary gel electrophoresis. These Group C block copolymers include: 30% $B_6E_{46}B_6$; 50% $B_6E_{46}B_6$; 60% $B_6E_{46}B_6$; 50% $B_5E_{91}B_5$; and 65% $E_{25}P_{40}E_{25}$. As Groups A, B and C copolymers indicate, good separation media are difficult to predict. Accordingly, the present invention sets forth copolymer media derived from empirical rules and testing.

In a further embodiment of the present invention, at least one of the block copolymers of the viscosity-adjustable medium is selected from the group consisting of $E_{41}B_8$, $E_{99}P_{69}E_{99}$, $B_{12}E_{260}B_{12}$, $E_{45}B_{14}E_{45}$, $E_{132}P_{56}E_{132}$, $E_{79}B_{36}E_{79}$, and mixtures thereof wherein E is poly (oxyethylene), P is poly(oxypropylene) and B is poly (oxybutylene).

In yet another embodiment of the present invention, the operating buffer is a good solvent for a first block segment of a block copolymer of the present invention and a marginal, poor or nonsolvent for a second block of the block copolymer. The marginally solvated, poorly solvated, or non-solvated block segments of the present invention self-assemble and form supramolecules. Beyond its overlap concentration, these supramolecules form gel-like networks through which charged molecules will migrate when an electric field is applied. In this way, the charged molecules are separated based on size and charge density.

Suitable operating buffers of the present invention include, for example, tris(hydroxymethyl)aminomethane, 2-N-(morpholine) ethanesulfonic acid, N-(2-acetamido) iminodiacetic acid, piperazine-N,N'-bis(2-ethanesulfonic acid, N(2-acetamido)-2-aminoethanesulfonic acid, (2-aminoethyl) trimethyl-ammonium chloride hydrochloride, N,N,-bis(2-hydroxy-ethyl)-2-aminoethane sulfonic acid, N-2-hydroxy-ethylpiperazine-N'-2-ethanesulfonic acid, N-tris(hydroxyl-methyl)methylglycine, N,N-bis(2-hydroxyethyl)-glycine, 2-(N-cyclohexylamino) ethanesulfonic acid and mixtures thereof. Preferably, the operating buffer is 1× TBE buffer which is about 89 mM tris(hydroxymethyl)aminomethane, about 89 mM boric acid, about 2 mM ethylenediaminetetraacetic acid (EDTA) in deionized water. In one embodiment of the present invention, the viscosity-adjustable medium includes about 25%(w/v) of $E_{99}P_{69}E_{99}$ in 1× TBE buffer.

As set forth hereinabove, the first operating temperature is a temperature outside of the normal operating temperature range for separation of charged molecules using, such as for example, electrophoresis. In one embodiment of the present invention, the first operating temperature is below the operating temperature of, e.g., electrophoresis. In this embodiment, the first operating temperature is below about 20° C. Preferably the first operating temperature is from about 15° C. to about 1° C. More preferably, the first operating temperature is about 4° C.

In another embodiment of the present invention, the first operating temperature is above the operating temperature of, for example, electrophoresis. Accordingly, in this embodiment a requirement with respect to the temperature range for the first operating temperature is that the viscosity-adjustable medium be in a liquid state and have a relatively low viscosity for easier fluid manipulation. Thus, the first operating temperature is determined by the physical properties of the particular block copolymers and operating buffer used. For example, a viscosity-adjustable medium composed of 15% (w/v) $E_{79}B_{36}E_{79}$ has a low solution viscosity at a first operating temperature of about 40° C. whereas it is gel-like at a second operating temperature of about 25° C.

For purposes of the present invention, the second operating temperature corresponds to that temperature at which the viscosity-adjustable medium forms a gel-like, polymer network. Like the first operating temperature, the second operating temperature is determined by the copolymer composition and the buffer used to make the viscosity-adjustable medium of the present invention. Preferably, the second operating temperature is above about 20° C.

Figure 5:
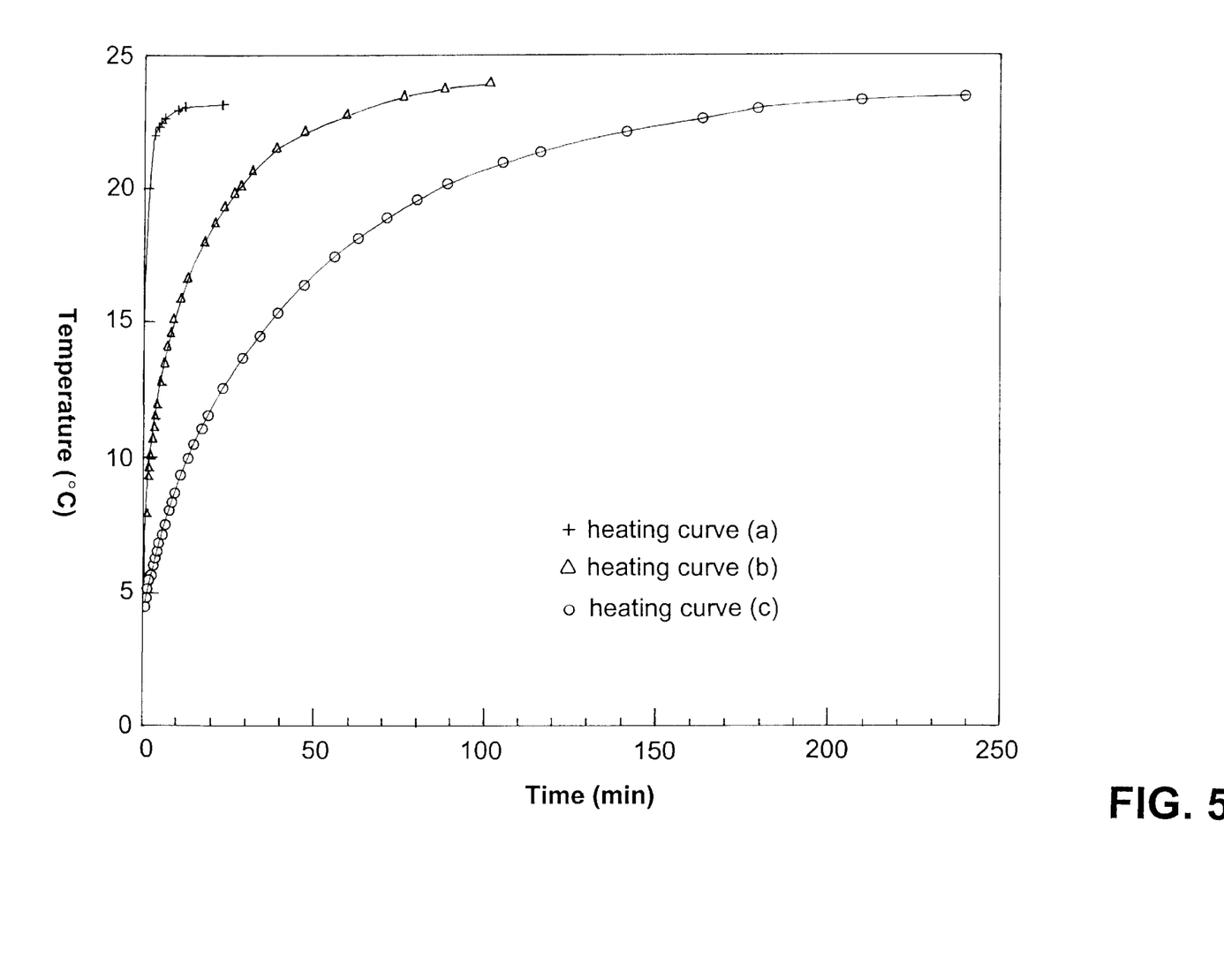
FIG. 5 shows heating curves of three preparations of the viscosity-adjustable matrix of FIG. 1.
Figure 6A:
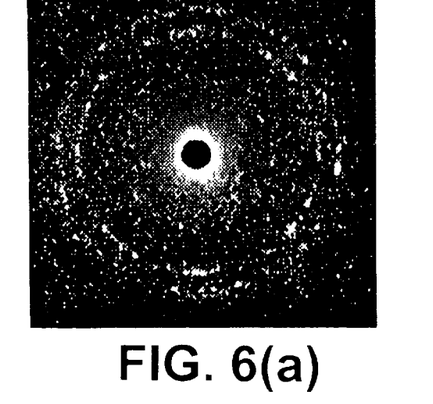
FIGS. 6a–6c show a synchrotron small angle x-ray scattering pictures of the three preparations of FIG. 5.
Figure 6B:
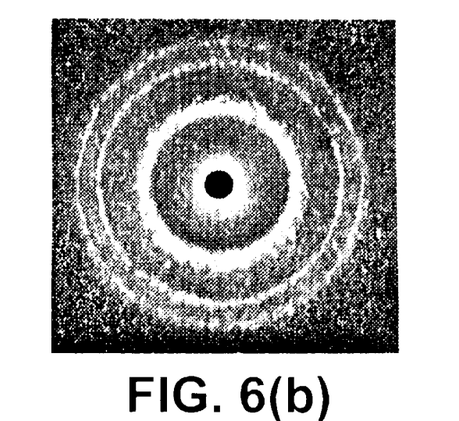
Figure 6C:
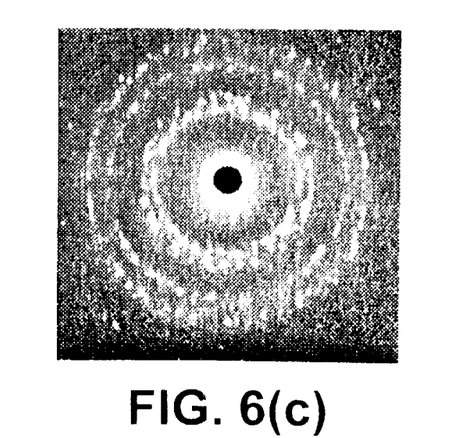

The rate at which the separation medium is brought from the first operating temperature to the second operating temperature effects the molecular order of the gel-like state. In particular, FIG. 5 shows heating curves of three separation media of 25% (w/v) F127 ($E_{99}F_{69}E_{99}$) as the temperature is raised from 4° C. to 25° C. at three different rates (a, b, and c). FIG. 6 shows a synchrotron small angle x-ray scattering (SAXS) picture of the molecular order of the three gels (a, b, c) after being subjected to the three different heating rates shown in FIG. 5. It is clear from FIG. 6 that the molecular structure of the gel-like state is more ordered with the slower heating rate. Furthermore, at higher operating temperatures, the molecular structure of certain compositions such as, for example, 25% (w/v) F127 of the present invention become more ordered.

Thus, the viscosity-adjustable medium according to the present invention finds utility as a separation medium for separating charged molecules in an electric field. The viscosity-adjustable medium of the present invention may be used in any separation method that utilizes the differential mobility of charged molecules in a medium under the influence of an electric field. Such separation methods include, for example, capillary electrophoresis and thin slab gel electrophoresis.

In yet another embodiment of the present invention, there is provided a system for conducting molecular separation. This system includes a capillary column that has an interior cavity which is defined by a wall with an inner surface and a composition containing one of the viscosity-adjustable media of the present invention disposed within the inner cavity of the capillary tube.

The capillary columns used in the present invention are well known in the art. For example, 13 cm long fused silica capillary tubes with an internal diameter (ID) of 100 µm and an outer diameter (OD) of 365 µm can be used. Such capillary tubes may optionally have their outer wall coated with polyimide.

In yet a further embodiment of the present invention, there is provided a method of separating charged molecules. This method includes introducing a separation medium containing one of the viscosity-adjustable block copolymers of the present invention into an inner cavity of a capillary column. The inner cavity of the capillary column is defined by a wall with an inner surface.

The separation medium which is at a first operating temperature can be introduced within the inner cavity of the capillary tube by conventional methods including for example, injection or pipetting. The temperature of the capillary tube and the separation medium is then brought to a second operating temperature wherein the separation medium becomes gel-like within the inner cavity of the capillary tube. The capillary tube containing the viscosity-adjustable medium is then connected to a standard capillary electrophoresis apparatus.

A sample containing charged molecules is then electrokinetically introduced into the gel-like medium. This sample may include DNA, RNA, protein and fragments thereof. An electric field is then applied to the gel-like medium and the sample is electrophoretically separated. The strength of the electric field will vary according to the nature of the sample to be separated, e.g., whether the sample is protein, DNA or RNA, the operating buffer used, the composition of the copolymer separation medium, the length of the column and the type of separation desired.

The separated sample is then detected according to well known methods in the art. See for example, Davis, L., Kuehl, M., and Battey, J. (1994) Basic Methods in Molecular Biology, 2nd edition, Appleton & Lange; Sambrook, J., Fritsch, E. F., and Maniatis, T. (1989) Molecular Cloning: A Laboratory Manual, 2nd edition, Cold Spring Harbor Laboratory Press; and Ausubel et al., Editors, (1987) Current Protocols in Molecular Biology, Green Publishing Associates and Wiley-Interscience. For example, ethidium bromide-stained DNA can be visualized under ultraviolet light or laser-induced fluorescence.

EXAMPLE 1

Preparation of F127 Block Copolymer

F127, a block copolymer of $E_{99}P_{69}E_{99}$, was prepared by adding 0.125 gm of F127 to 0.5 ml of 1× TBE buffer. The solution was stirred in an ice bath for about 1 hr. The foamy solution was then stored at 4° C. for several days before use.

EXAMPLE 2

Separation of DNA With F127 Block Copolymer

φX174RF DNA-Hae III digest (New England Biolabs, Inc., Beverley, Mass.), pBR322 DNA-BstN I digest (New England Biolabs, Inc., Beverley, Mass.), φX174RF DNA-Hinc II digest (Pharmacia LKB Biotechnology, Inc., Piscataway, N.J.) and oligonucleotide sizing markers (Pharmacia LKB Biotechnology, Inc., Piscataway, N.J.) were prepared as follows: φX174 DNA-Hae III digest, pBR322 DNA-BstN I digest, and φX174RF DNA-Hinc II digest were each diluted to 10 µg/ml using 1× TE buffer (10 mM Tris-HCl, pH 7.4, 0.1 mM EDTA). The synthetic oligonucleotide sizing marker was diluted ten times with deionized water to a final concentration of 1.6 µg/ml.

A 13 cm long fused silica capillary tube (Polymicro Technologies, Phoenix, Ariz.) with ID/OD=98 µm/364 µm was flushed with 1 ml of 1 N HCl for about 10 minutes. A detection window of about 2 mm width was opened at a point 10 cm from the cathodic end of the capillary tube by stripping the polyimide coating off with a razor blade.

Cathode and anode reservoirs each having 2.6 ml capacity were filled with a running buffer of 1 µg/ml ethidium bromide (Sigma Chemical Co., St. Louis, Mo.) in 1× TBE.

The F127 block copolymer solution according to Example 1 at a temperature of 4° C. was then injected into the capillary tube using a 50 µl syringe. The capillary tube was then attached to a capillary electrophoresis apparatus and the temperature of the capillary tube was raised to room temperature. In about 10 minutes, the F127 block copolymer solution changed to its gel-like state.

The F127 block copolymer was then subjected to a constant electric field strength of about 200 V/cm for about 25–30 minutes in order to introduce a fluorescent dye into the gel-like material and to stabilize the current. A DNA sample as described in Example 1 was nelectrokinetically injected into the capillary tubing at an electric field strength of about 300 V/cm for about 5 seconds. The run time electric field strength was about 200 V/cm. The DNA was separated for about 40 minutes. A new separation medium was used for each DNA sample tested.

The voltage for the electric current was generated by two computer-controlled Quatech interface boards, a WSB-100 digital pattern generator adapter, a WSB-A12M waveform synthesizer module and a Trek PM0610 amplifier. A custom-built laser-induced fluorescence capillary electrophoresis instrument was used to detect the separated DNA fragments. This instrument used an argon-ion laser operating at a wavelength of about 488 nm with a 5 mW output power. The fluorescence produced from the DNA-ethidium bromide complex was detected using a Zeiss epillumination fluorescence microscope and a Hamamatsu R928 photomultiplier tube.

After detection of the separated DNA fragments, the state of the F127 block copolymer material was changed from the gel-like state back to the solution state by lowering the temperature to 4° C. The F127 block copolymer solution was then extruded from the capillary tube using 1 ml of distilled water. The capillary tube was then treated with 1 ml of 1 N HCl for 10 minutes. The capillary tube was then ready for introduction of another copolymer solution.

EXAMPLE 3

Separation of dsDNA with F127 Block Copolymer

A viscosity-adjustable separation medium of 25% (w/v) $E_{99}P_{69}E_{99}$ was prepared as described in Example 1. The low viscosity $E_{99}P_{69}E_{99}$ separation medium was injected into a 13 cm long capillary tube having an ID/OD=98 $\mu$m/364 $\mu$m. The $E_{99}P_{69}E_{99}$ separation medium was brought to about 25° C. where it became gel-like.

Samples of double stranded DNA (dsDNA) were prepared according to Example 2 with the following modifications. dsDNA samples of $\phi$X174RF DNA-Hae III and pBR322 DNA-BstN I digests were combined and diluted to 10 $\mu$g/ml using 1× TE buffer as described in Example 2.

Figure 1:
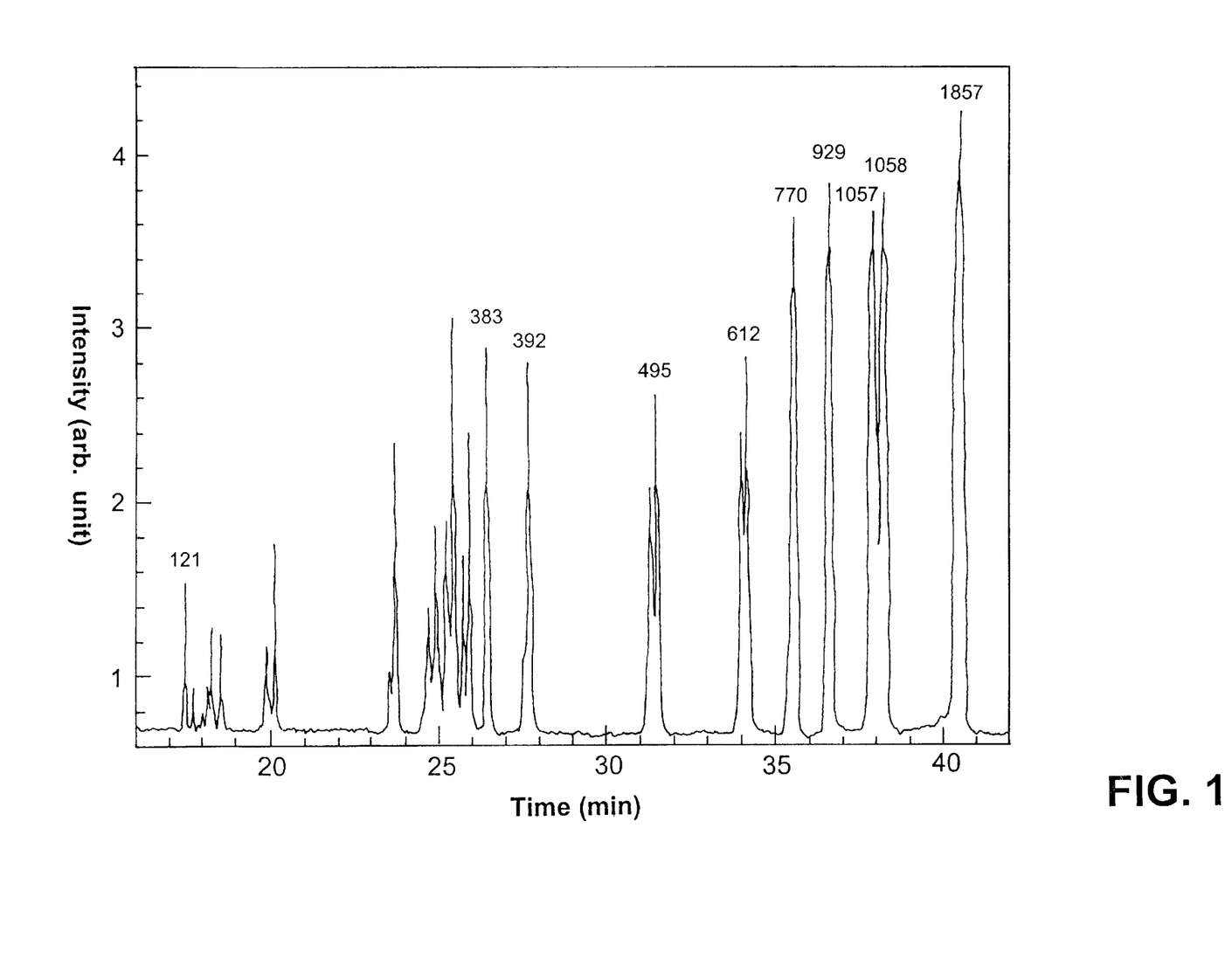
FIG. 1 shows an electropherogram of dsDNA separated on a viscosity-adjustable matrix of $E_{99}P_{69}E_{99}$.

The $E_{99}P_{69}E_{99}$ separation medium was equilibrated under 200 V/cm as described in Example 2. The dsDNA sample was electrokinetically injected into the $E_{99}P_{69}E_{99}$ separation medium and separated as described in Example 2. FIG. 1 is an electropherogram of this separation which shows the high degree of resolution achievable with the separation medium of the present invention. In particular, the 1057 and 1058 base pair peaks demonstrate that the $E_{99}P_{69}E_{99}$ separation medium is able to achieve 1 base pair resolution with dsDNA fragments in the 1000 base-pair range.

EXAMPLE 4

Separation of ssDNA with $B_{12E}E_{260}B_{12}$ Block Copolymer

Figure 2:
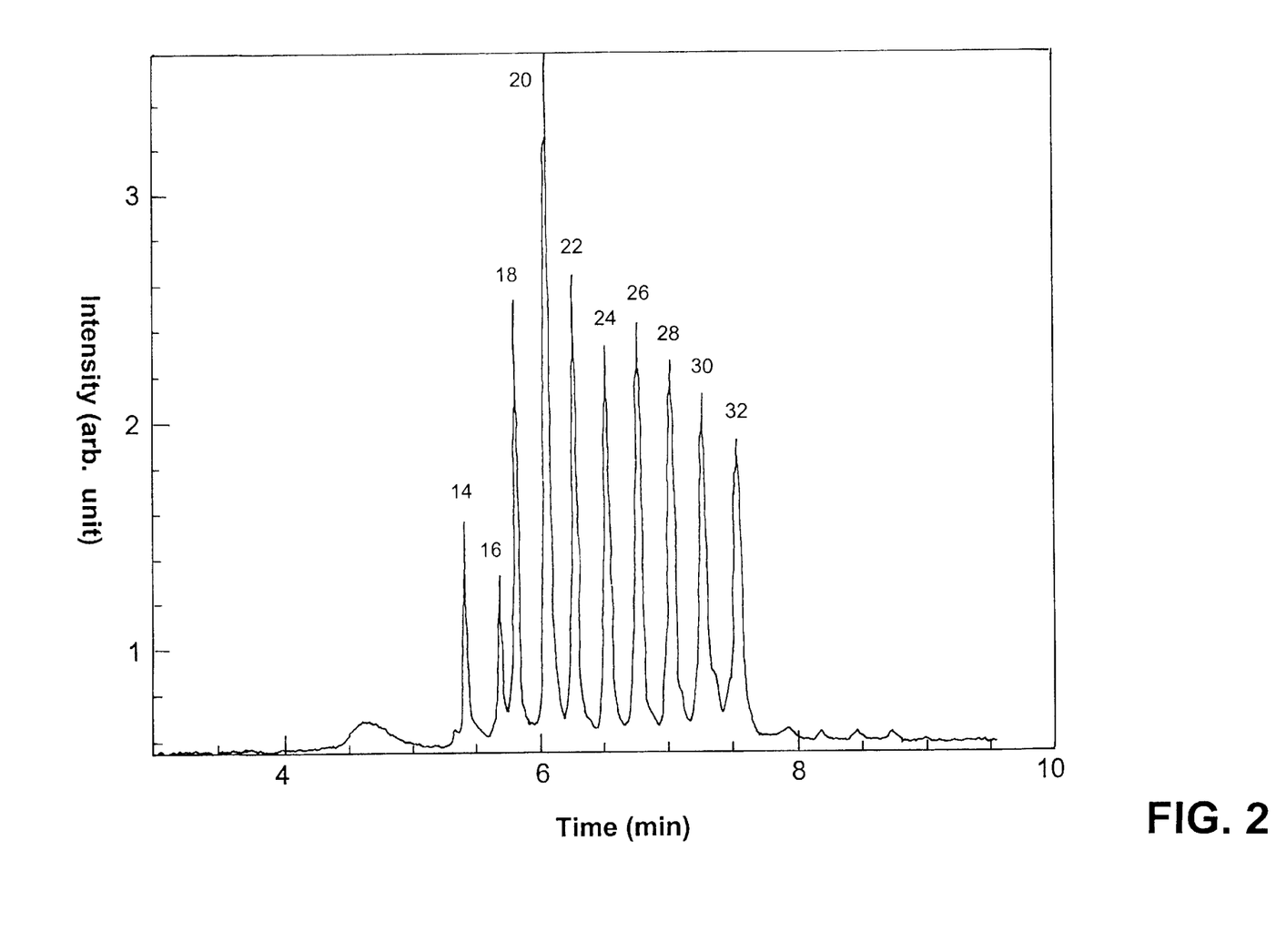
FIG. 2 shows an electropherogram of ssDNA separated on a viscosity-adjustable matrix of $B_{12}E_{260}B_{12}$.

Using a 10% (w/v) $B_{12}E_{260}B_{12}$ separation medium according to the present invention, single stranded DNA (ssDNA) was separated and detected as is shown in the electropherogram of FIG. 2.

The ssDNA oligonucleotide markers were prepared as described in Example 2. The ssDNA oligonucleotide markers were separated on the $B_{12}E_{260}B_{12}$ separation medium as described in Example 3. FIG. 2 shows an electropherogram of this separation which demonstrates the high resolution achievable with the $B_{12}E_{260}B_{12}$ separation medium as is evidenced by, for example, the peaks at 22 and 24 bases.

EXAMPLE 5

Separation of ssDNA with F127 Block Copolymer

Figure 3:
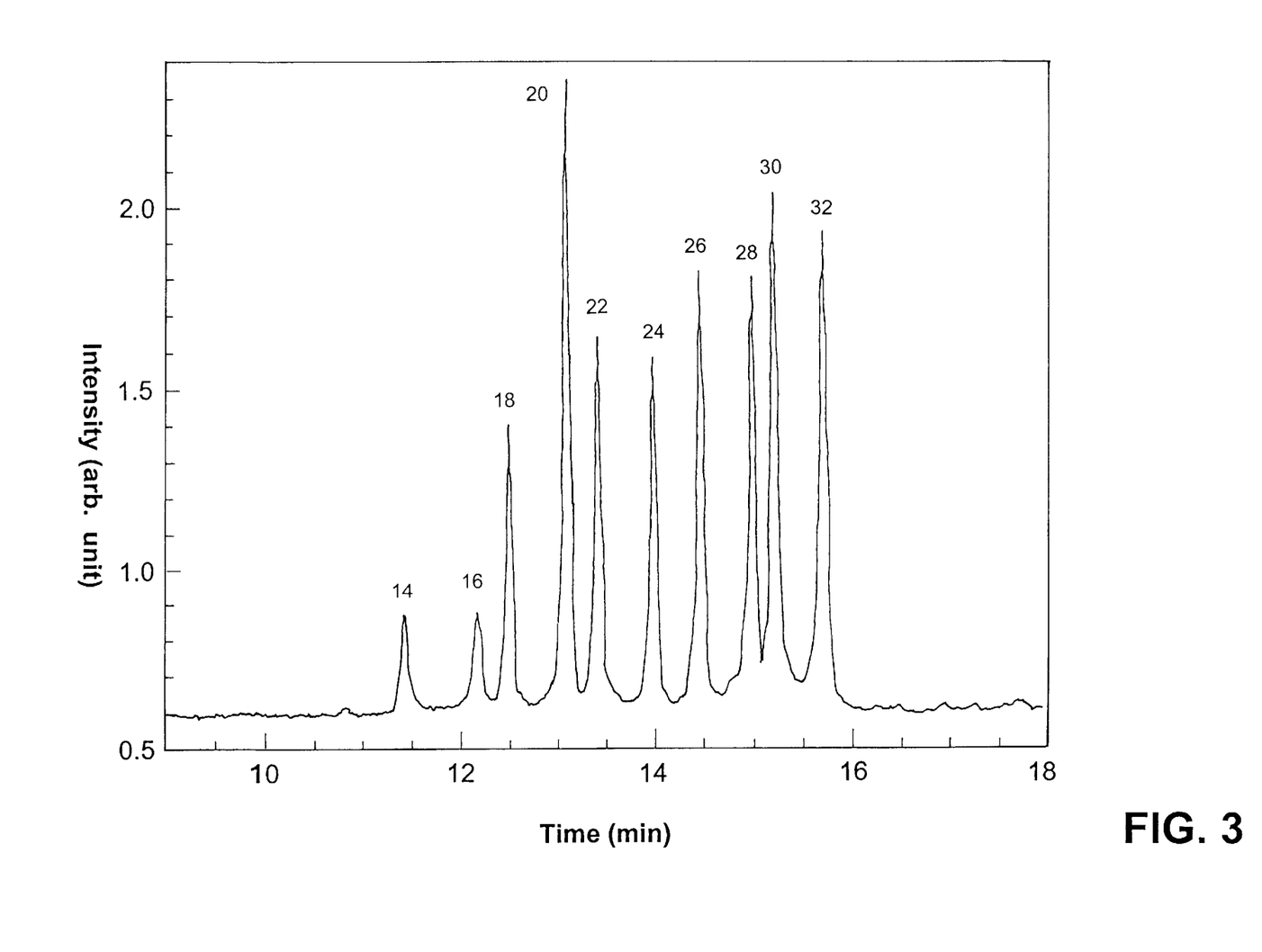
FIG. 3 shows an electropherogram of ssDNA separated on the viscosity-adjustable matrix of FIG. 1.

Using F127 ($E_{99}P_{69}E_{99}$) as a separation medium, ssDNA of oligonucleotide sizing markers were separated as described in Example 4. FIG. 3 shows an electropherogram of this separation which demonstrates the high degree of resolution achievable with $E_{99}P_{69}E_{99}$ separation medium as is evidenced by, for example, the peaks at 22 and 24 bases.

EXAMPLE 6

Separation of 9.6 kD Protein with F-127 Block Copolymer

Using a 25% (w/v) $E_{99}P_{69}E_{99}$ separation medium according to the present invention, a 89 amino acid (9,642 D) fragment of the globular domain of Histone-5 protein was separated. This histone protein fragment was labeled with fluorescein isothiocyanate for visualization purposes. The separation procedure was substantially as described in Example 2 with the following modifications.

Figure 4:
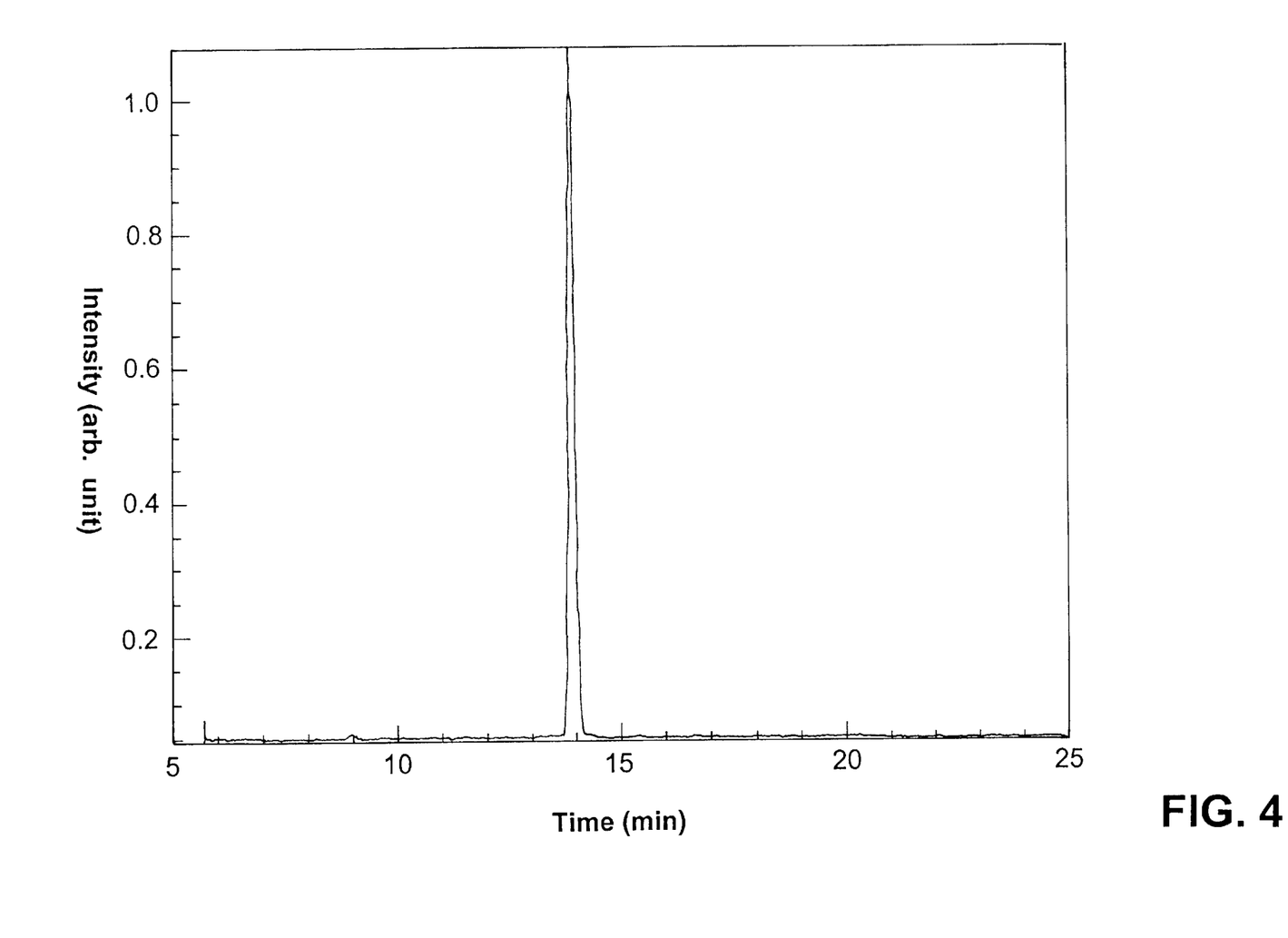
FIG. 4 shows an electropherogram of a 9.6 kD histone protein fragment separated on the viscosity-adjustable matrix of FIG. 1.

The operating buffer used in this Example was 1× Tris-Glycine which is about 25 mM Tris and about 192 mM Glycine. The electric field used in the separation was 200 V/cm. The electropherogram of FIG. 4 shows the rapid and high resolution separation of proteins achievable with the separation media of the present invention.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A viscosity-adjustable medium for use in separation methods comprising:

a) a first block copolymer comprising a poly(oxybutylene) block segment, which dynamically disassembles to be in solution at a first operating temperature, and which dynamically self-assembles to be in a gel-like state at a second operating temperature, said block copolymer forming microstructure networks which are effective for separating charged molecules in said gel-like state; and b) a second block copolymer which has the same properties as said first block copolymer and is selected to combine with said first block copolymer to form said viscosity-adjustable medium;

c) an operating buffer which dissolves said first and second block copolymers at said first operating temperature and which remains in said medium in said gel-like state without disruption of said separation method, said buffer rendering said block copolymers dissolute upon return to said first operating temperature.

2. The medium according to claim 1 wherein said first and second block copolymers are selected from the group consisting of di-block copolymers, tri-block copolymers, multi-block copolymers and mixtures thereof.

3. The medium according to claim 1 wherein said first and second block copolymers are described by $A_xB_y;$  Formula (I)

$A_xB_yA_z;$  Formula (II)

$$B_xA_yB_z;\quad \text{Formula (III)}$$

$$A_xB_yC_z;\quad \text{Formula (IV)}$$

and mixtures thereof, wherein A, B and C are block segments and wherein A, B or C is poly(oxybutylene) and the remaining block segment or segments are independently selected from the group consisting of poly(oxyethylene), poly(oxypropylene), polyacrylamide and poly(isopropyl) acrylamide; and x, y, and z are independently selected from whole numbers from about 1–10,000.

4. The medium according to claim 1 wherein at least one of said first and second block copolymers is selected from the group consisting of $E_{41}B_8$, $B_{12}E_{260}B_{12}$, $E_{41}B_8$, $E_{45}B_{14}E_{45}$, $E_{79}B_{36}E_{79}$, and mixtures thereof wherein E is poly(oxyethylene) and B is poly(oxybutylene).

5. The medium according to claim 1 wherein said operating buffer is a good solvent for a first block segment of said first and second block copolymers and is a marginal solvent, a poor solvent or a nonsolvent for a second block of said first and second block copolymers.

6. The medium according to claim 5 wherein nonsolvated block segments of said first and second block copolymers self-assemble into said gel-like state.

7. The medium according to claim 1 wherein said operating buffer is selected from the group consisting of 1× TBE and tris-glycine buffers.

8. The medium according to claim 1 wherein said first operating temperature is a temperature which is not destructive of said first and second block copolymers and which is characterized by a low viscosity of said block copolymers.

9. The medium according to claim 1 wherein said second operating temperature is a temperature which is not destructive of said first and second block copolymers.

10. The medium according to claim 1 wherein said first operating temperature is from about 15° C. to about 1° C.

11. The medium according to claim 1 wherein said second operating temperature is above about 20° C.

12. The medium according to claim 1 wherein said separation methods are selected from the group consisting of capillary electrophoresis and thin slab gel electrophoresis.

13. A system for conducting molecular separation comprising:
a) a capillary column having an interior cavity defined by a wall with an inner surface; and
b) a composition disposed within said interior cavity, said composition comprising at least one block copolymer comprising a poly(oxybutylene) block segment, which dynamically disassembles to be in solution at a first operating temperature and which dynamically self-assembles to be in a gel-like state at a second operating temperature, and an operating buffer which dissolves said at least one block copolymer at said first operating temperature and which remains in said medium in said gel-like state without disruption of said separation method, said buffer rendering said at least one block copolymer dissolute upon return to said first operating temperature, said block copolymer forming microstructure networks which are effective for separating charged molecules in said gel-like state.

14. The system according to claim 13 wherein said block copolymer is described by $$A_xB_y;\quad \text{Formula (I)}$$

$$A_xB_yA_z;\quad \text{Formula (II)}$$

$$B_xA_yB_z;\quad \text{Formula (III)}$$

$$A_xB_yC_z;\quad \text{Formula (IV)}$$

and mixtures thereof, wherein A, B and C are block segments and wherein A, B or C is poly(oxybutylene) and the remaining block segment or segments are independently selected from the group consisting of poly(oxyethylene), poly(oxypropylene), polyacrylamide and poly(isopropyl) acrylamide; and x, y, and z are independently selected from whole numbers from about 1–10,000.

15. The system according to claim 13 wherein said operating buffer is selected from the group consisting of 1× TBE and tris-glycine buffers.

16. A method of separating charged molecules comprising:
a) introducing a separation medium into an interior cavity of a capillary column which is defined by a wall with an inner surface, said separation medium comprising at least one block copolymer comprising a poly(oxybutylene) block segment, which dynamically disassembles to be in solution at a first operating temperature and which dynamically self-assembles to be in a gel-like state at a second operating temperature, said block copolymer forming microstructure networks which are effective for separating charged molecules in said gel-like state and an operating buffer which dissolves said at least one block copolymer at said first operating temperature and which remains in said medium in said gel-like state without disruption of said separation method, said buffer rendering said at least one block copolymer dissolute upon return to said first operating temperature;
b) changing the temperature of said separation medium from the first operating temperature to the second operating temperature which renders said separation medium gel-like within said interior cavity;
c) injecting a sample containing materials to be separated into said gel-like state;
d) separating said sample into its constituent components; and
e) detecting said constituents of said sample.

17. The method according to claim 16 wherein said block copolymer is selected from the group consisting of di-block copolymers, tri-block copolymers, multi-block copolymers and mixtures thereof.

18. The method according to claim 16 wherein said block copolymer is described by $$A_xB_y;\quad \text{Formula (I)}$$

$$A_xB_yA_z;\quad \text{Formula (II)}$$

$$B_xA_yB_z;\quad \text{Formula (III)}$$

$$A_xB_yC_z;\quad \text{Formula (IV)}$$

and mixtures thereof, wherein A, B and C are block segments and wherein A, B or C is poly(oxybutylene) and the remaining block segment or segments are independently selected from the group consisting of poly(oxyethylene), poly(oxypropylene), polyacrylamide and poly(isopropyl) acrylamide; and x, y, and z are independently selected from whole numbers from about 1–10,000.

* * * * *